(12) United States Patent
Manaka

(10) Patent No.: US 12,194,456 B2
(45) Date of Patent: Jan. 14, 2025

(54) BLOOD COLLECTION TUBE HOLDER AND BLOOD COLLECTION KIT

(71) Applicant: KABUSHIKI KAISHA TOP, Tokyo (JP)

(72) Inventor: Yuki Manaka, Tokyo (JP)

(73) Assignee: KABUSHIKI KAISHA TOP, Tokyo (JP)

( * ) Notice: Subject to any disclaimer, the term of this patent is extended or adjusted under 35 U.S.C. 154(b) by 652 days.

(21) Appl. No.: 17/617,910

(22) PCT Filed: Jun. 8, 2020

(86) PCT No.: PCT/JP2020/022555
§ 371 (c)(1),
(2) Date: Dec. 9, 2021

(87) PCT Pub. No.: WO2020/250852
PCT Pub. Date: Dec. 17, 2020

(65) Prior Publication Data
US 2022/0305486 A1     Sep. 29, 2022

(30) Foreign Application Priority Data

Jun. 13, 2019 (JP) .................................. 2019-110181
Feb. 21, 2020 (JP) .................................. 2020-028675

(51) Int. Cl.
*B01L 3/00*     (2006.01)
(52) U.S. Cl.
CPC .......... *B01L 3/502* (2013.01); *B01L 2200/026* (2013.01); *B01L 2200/04* (2013.01);
(Continued)

(58) Field of Classification Search
CPC .......... A61B 5/15003; A61B 5/150389; A61B 5/150473; A61B 5/150572;
(Continued)

(56) References Cited

U.S. PATENT DOCUMENTS 4,320,769 A   3/1982  Eichhorn et al.
5,776,076 A   7/1998  Chen
(Continued)

FOREIGN PATENT DOCUMENTS

EP    1 782 732 A1    5/2007
JP    S58-038941 U   3/1983
(Continued)

OTHER PUBLICATIONS

JP H07-204180 A English translation (Year: 2024).*
(Continued)

*Primary Examiner* — Jennifer Wecker
*Assistant Examiner* — Jonathan Bortoli
(74) *Attorney, Agent, or Firm* — Rankin, Hill & Clark LLP

(57) ABSTRACT

A blood collection tube holder that prevents a blood collection tube from falling even when pressed by an elastic sheath body being compressed is provided. A blood collection tube holder 1 includes a blood collection tube holder body 11 and a holding member 12. The blood collection tube holder body 11 includes a needle tube 17 supported by a needle base 15, and an elastic sheath body 18 covering the needle tube 17, and the holding member 12 includes a press-contact member 22. The blood collection tube holder body 11 includes a tongue-shaped protrusion piece 20.

21 Claims, 12 Drawing Sheets

(52) U.S. Cl.
CPC ............. *B01L 2300/0609* (2013.01); *B01L 2300/0672* (2013.01); *B01L 2300/123* (2013.01)

(58) Field of Classification Search
CPC .. A61B 5/150992; A61B 5/154; A61M 39/10; A61M 5/3257; A61M 5/158; B01L 2200/026; B01L 2200/04; B01L 2300/0609; B01L 2300/0672; B01L 2300/123; B01L 3/502
See application file for complete search history.

(56) References Cited

U.S. PATENT DOCUMENTS

| | | |
|---|---|---|
| 2006/0009714 A1 | 1/2006 | Higaki et al. |
| 2016/0100784 A1 | 4/2016 | Kashmirian |
| 2018/0192933 A1 | 7/2018 | Anitua Aldecoa |

FOREIGN PATENT DOCUMENTS

| | | | |
|---|---|---|---|
| JP | H05-051308 U | | 7/1993 |
| JP | H05-300899 A | | 11/1993 |
| JP | H06-038945 A | | 2/1994 |
| JP | H07204180 A | * | 8/1995 |
| JP | H07-327963 A | | 12/1995 |
| JP | 2001-527438 A | | 12/2001 |
| JP | 2002-291724 A | | 10/2002 |
| JP | 2007-75385 A | | 3/2007 |
| JP | 2007-152083 A | | 6/2007 |
| JP | 3179889 U | | 11/2012 |
| JP | 2018-93888 A | | 6/2018 |
| WO | 2007/134347 A2 | | 11/2007 |
| WO | 2017/086867 A1 | | 5/2017 |
| WO | 2018/216272 A1 | | 11/2018 |

OTHER PUBLICATIONS

Japanese Office Action issued Jul. 31, 2023 in corresponding Japanese application No. 2021-131012; English translation included (8 pages).
Indian Office Action dated Sep. 21, 2023 issued in corresponding Indian application No. 202117058374; English translation included (5 pages).
Extended European Search Report dated Dec. 15, 2022 issued in corresponding European application No. 20821708.3 (7 pages).
International Search Report dated Aug. 18, 2020, 3 pages.

* cited by examiner

BLOOD COLLECTION TUBE HOLDER AND BLOOD COLLECTION KIT

TECHNICAL FIELD

The present invention relates to a blood collection tube holder and a blood collection kit.

BACKGROUND ART

Conventionally, a blood collection kit has been used to collect a blood specimen for a blood examination or the like. The blood collection kit collects blood from a living body with a blood collection member such as what is called a butterfly needle (winged needle) including a needle tube with which a blood vessel is pierced, and accumulates the collected blood specimen in a vacuum blood collection tube held on a blood collection tube holder, the blood collection kit including the blood collection member and a blood collection tube holder that is connected to the blood collection member through a connector and holds the vacuum blood collection tube.

For example, a known blood collection tube holder includes a blood collection tube holder body having a hollow bottomed cylindrical shape, and a holding member that is internally fitted to an inner peripheral surface of the blood collection tube holder body and detachably holds a blood collection tube such as a syringe inserted into a hollow part of the blood collection tube holder body (refer to Patent Literature 1, for example).

The blood collection tube holder disclosed in Patent Literature 1 includes a hollow needle tube that is supported by a needle base mounted on a bottom part of the blood collection tube holder body and protrudes the hollow part of the blood collection tube holder body, and when the blood collection tube such as a syringe is inserted into the hollow part of the blood collection tube holder body, the needle tube penetrates the blood collection tube, and a collected blood specimen is introduced into the blood collection tube through the needle tube. In the blood collection tube holder disclosed in Patent Literature 1, the holding member includes a plurality of press-contact members, and when the blood collection tube such as a syringe is inserted into the hollow part of the blood collection tube holder body, the press-contact member swings toward the inner peripheral surface of the blood collection tube holder body and is pressed to contact an outer peripheral surface of the blood collection tube by elastic force of the press-contact member. As a result, while the collected blood specimen is introduced into the blood collection tube, the blood collection tube holder holds the blood collection tube with the press-contact member being pressed to contact the outer peripheral surface of the blood collection tube, thereby preventing the blood collection tube from falling off the hollow part of the blood collection tube holder body.

CITATION LIST

Patent Literature

Patent Literature 1
Japanese Patent Laid-Open No. 5-300899

SUMMARY OF INVENTION

Technical Problem

However, in the blood collection tube holder disclosed in Patent Literature 1, when the blood collection tube is inserted into the hollow part of the blood collection tube holder body, an elastic sheath body covering the needle tube is pressed and compressed by a leading end part of the blood collection tube, and as the elastic sheath body returns to the original form by its elasticity, the blood collection tube is pressed by the elastic sheath body and potentially falls off the blood collection tube holder body, which has been a disadvantage.

An object of the present invention is to solve the above-described disadvantage and provide a blood collection tube holder that prevents the blood collection tube from falling even when pressed by the elastic sheath body being compressed.

Solution to Problem

To achieve the above-described intention, a blood collection tube holder of the present invention includes: a blood collection tube holder body having a hollow bottomed tubular shape; and a holding member that is internally fitted to an inner peripheral surface of the blood collection tube holder body and detachably holds a blood collection tube that is inserted into a hollow part of the blood collection tube holder body, the blood collection tube holder body includes a needle base provided at a bottom part, a hollow needle tube supported by the needle base and protruding into the hollow part of the blood collection tube holder body, and an elastic sheath body covering the needle tube across an entire length of the needle tube, the holding member includes a fitting member that has a hollow tubular shape and is internally fitted to the inner peripheral surface of the blood collection tube holder body, and a plurality of press-contact members that protrude from the fitting member into the hollow part of the blood collection tube holder body and that swing toward the inner peripheral surface of the blood collection tube holder body and are pressed to contact an outer peripheral surface of the blood collection tube by elastic force of the press-contact members when the blood collection tube is inserted into the hollow part of the blood collection tube holder body, the blood collection tube holder body includes a plurality of tongue-shaped protrusion pieces protruding into the hollow part of the blood collection tube holder body, and when the blood collection tube is inserted into the hollow part of the blood collection tube holder body and the press-contact members swing toward the inner peripheral surface of the blood collection tube holder body, the tongue-shaped protrusion pieces contact leading ends of the press-contact members, swing toward the inner peripheral surface of the blood collection tube holder body, and assist, with elastic force of the tongue-shaped protrusion pieces, the press-contact of the press-contact members with the outer peripheral surface of the blood collection tube.

A blood collection kit of the present invention includes: the blood collection tube holder of the present invention; and a blood collection member including a blood collection needle tube with which a blood vessel is pierced and a holder-side connector, the holder-side connector being connectable to the blood collection tube holder body so that the blood collection needle tube and the needle tube communicate with each other.

In the blood collection tube holder and the blood collection kit of the present invention, when the blood collection tube is inserted into the hollow part of the blood collection tube holder body, the plurality of press-contact members that protrude from the fitting member of the holding member into the hollow part of the blood collection tube holder body are pressed by the blood collection tube and swing toward the inner peripheral surface of the blood collection tube holder body. In this case, upon swinging as described above, each press-contact member is pressed to contact the outer peripheral surface of the blood collection tube as returning to the original form by elastic force of the press-contact member, thereby holding the blood collection tube.

When the blood collection tube is inserted into the hollow part of the blood collection tube holder body, the elastic sheath body is pressed by a leading end part of the blood collection tube and the needle tube penetrates the elastic sheath body and is inserted into the blood collection tube, and also the elastic sheath body is compressed between the bottom part of the blood collection tube holder body and the leading end part of the blood collection tube. The elastic sheath body being compressed presses the blood collection tube toward a back side (opening side) as returning to the original form by elastic force of the elastic sheath body.

In this case, in the blood collection tube holder and the blood collection kit of the present invention, the blood collection tube holder body includes the plurality of tongue-shaped protrusion pieces protruding into the hollow part of the blood collection tube holder body, and the tongue-shaped protrusion pieces contact leading ends of the press-contact members being pressed by the blood collection tube and swinging toward the inner peripheral surface of the blood collection tube holder body, and swing toward the inner peripheral surface of the blood collection tube holder body. When swinging as described above, each tongue-shaped protrusion piece presses the leading end of the corresponding press-contact member toward the outer peripheral surface of the blood collection tube as returning to the original form by elastic force of the tongue-shaped protrusion piece.

As a result, press-contact of each press-contact member with the outer peripheral surface of the blood collection tube is assisted by pressing force of the corresponding tongue-shaped protrusion piece in addition to elastic force of the press-contact member, and thus the blood collection tube can be held with stronger force, thereby preventing the blood collection tube from falling when pressed by the elastic sheath body being compressed.

However, depending on the size of the diameter of the blood collection tube, elastic force with which the holding member returns to the original form is not sufficiently obtained, and press-contact with the outer peripheral surface of the blood collection tube is insufficient in some cases.

Thus, in the blood collection tube holder of the present invention, it is preferable that each press-contact member includes an arm-shaped part protruding from the fitting member toward a central axis of the hollow part of the blood collection tube holder body, a bend part bending from a leading end part of the arm-shaped part toward the inner peripheral surface of the blood collection tube holder body, and at least one of a first reinforcement piece and a second reinforcement piece, the first reinforcement piece connecting the fitting member and the arm-shaped part, the second reinforcement piece connecting the arm-shaped part and the bend part.

In the blood collection tube holder of the present invention, since each press-contact member includes the first reinforcement piece or the second reinforcement piece, elastic force that causes return to the original form can be sufficiently obtained even when the diameter of the blood collection tube is small, and the blood collection tube can be held by reliable press-contact with the outer peripheral surface of the blood collection tube.

In the blood collection tube holder of the present invention, it is preferable that the blood collection tube holder body includes, on the inner peripheral surface of the blood collection tube holder body, a plurality of contact parts that contact the outer peripheral surface of the blood collection tube inserted into the hollow part of the blood collection tube holder body. With this configuration, it is possible to prevent tilt of the blood collection tube relative to the blood collection tube holder body so that the needle tube appropriately penetrates the blood collection tube, and stably hold the blood collection tube.

In the blood collection tube holder of the present invention, it is preferable that at least some of the plurality of contact parts each include a lock part that prevents fall of the blood collection tube by being locked to a flange part included in the blood collection tube inserted into the hollow part of the blood collection tube holder body. With this configuration, when the blood collection tube is pressed by the elastic sheath body being compressed, the lock part is locked to the flange part, thereby more reliably preventing fall of the blood collection tube.

In the blood collection tube holder of the present invention, it is preferable that each press-contact member includes a lock part that prevents fall of the blood collection tube by being locked to a flange part included in the blood collection tube inserted into the hollow part of the blood collection tube holder body. With this configuration, when the blood collection tube is pressed by the elastic sheath body being compressed, the lock part is locked to the flange part, thereby more reliably preventing fall of the blood collection tube.

In the blood collection tube holder of the present invention, it is preferable that the blood collection tube holder body includes, on the inner peripheral surface of the blood collection tube holder body, at least one of a first recessed part in which at least part of the fitting member is housed and a second recessed part in which at least part of a corresponding one of the press-contact members or a corresponding one of the tongue-shaped protrusion pieces swinging toward the inner peripheral surface of the blood collection tube holder body is housed. With this configuration, the outer diameter of the blood collection tube holder body can be reduced to improve grasping easiness and operating easiness while the blood collection tube can be reliably held by the holding member.

In the blood collection tube holder of the present invention, the blood collection tube holder body may include a connector that is connectable to a syringe so that the syringe and the needle tube communicate with each other. With this configuration, when a blood specimen collected in the syringe is to be dispensed to the blood collection tube, the blood collection needle tube connected to the syringe does not need penetrate the blood collection tube, and thus it is possible to reduce a risk of needle sticking at dispensing and safely perform dispensing.

The blood collection kit of the present invention may include: the blood collection tube holder of the present invention; and a connection member including a syringe-side connector and a holder-side connector, the syringe-side connector being connectable to a syringe, the holder-side connector being connectable to the blood collection tube holder body so that the syringe connected to the syringe-side connector and the needle tube communicate with each other. With this configuration, when a blood specimen collected in the syringe is to be dispensed to the blood collection tube, the blood collection needle tube connected to the syringe does not need to penetrate the blood collection tube, and thus it is possible to reduce a risk of needle sticking at dispensing and safely perform dispensing.

DESCRIPTION OF EMBODIMENT

An embodiment of the present invention will be described below in further detail with reference to the accompanying drawings.

Figure 1:
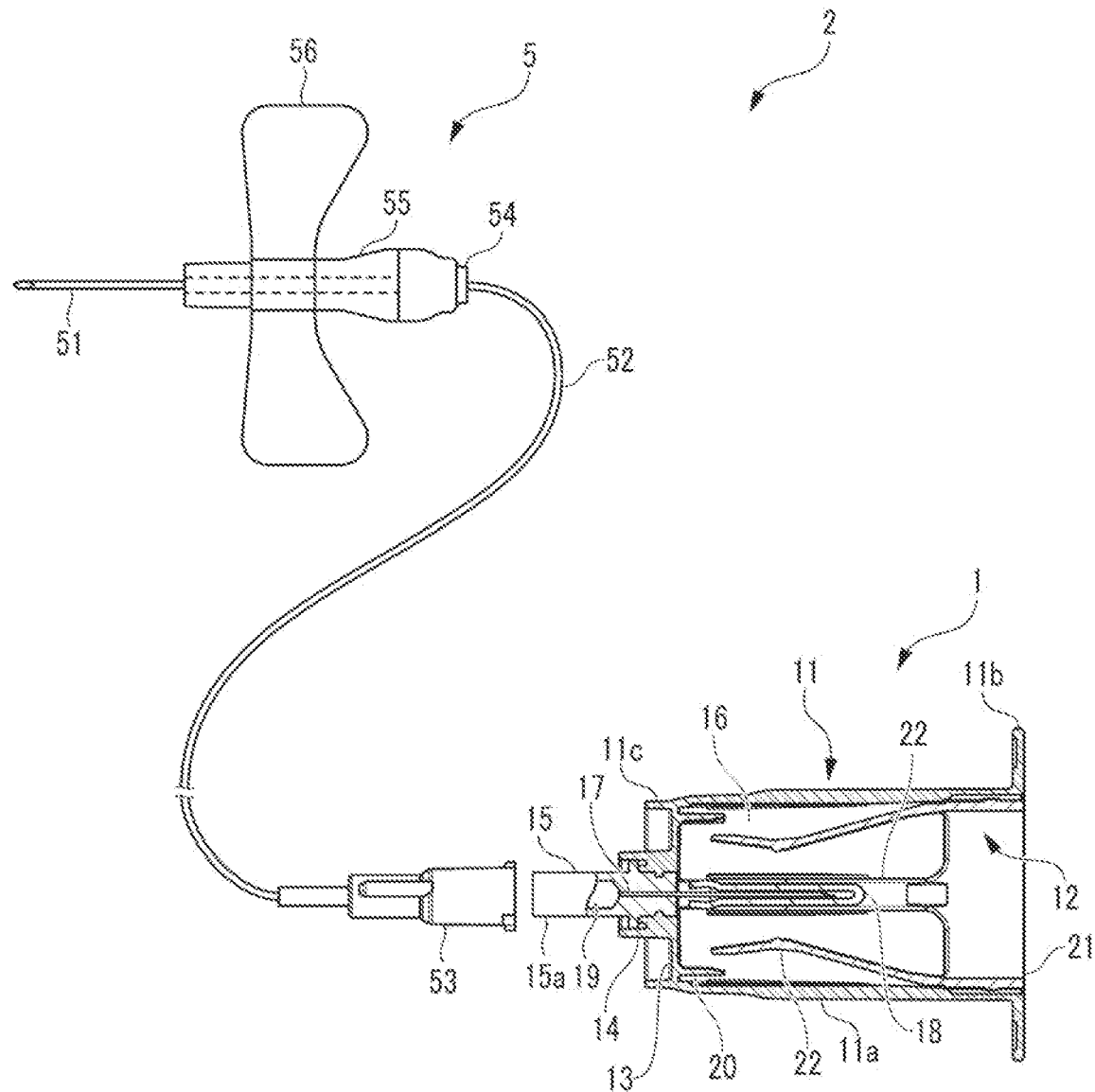
FIG. 1 is an explanatory diagram illustrating an exemplary configuration of a blood collection tube holder and a blood collection kit of the present invention.

As illustrated in FIG. 1, a blood collection tube holder 1 of the present embodiment is part of the configuration of a blood collection kit 2, is used to hold a vacuum blood collection tube (not illustrated) in which a blood specimen collected by the blood collection kit 2 is accumulated, and includes a blood collection tube holder body 11 having a hollow bottomed cylindrical shape, and a holding member 12 configured to detachably hold the vacuum blood collection tube.

The blood collection kit 2 of the present embodiment includes the blood collection tube holder 1, and a blood collection member 5 that is fixed to a living body while a blood vessel is pierced with the blood collection member 5. The blood collection member 5 includes a hollow blood collection needle tube 51 that has a sharp leading end and with which a blood vessel is pierced, a flexible tube 52 connected to a base end part of the blood collection needle tube 51, and a female connector 53 (holder-side connector of the present invention) connected to a base end part of the flexible tube 52.

In the present embodiment, the blood collection needle tube 51 is supported by a hub 54 to which a leading end part of the flexible tube 52 is connected, and a tubular protector 55 that covers a leading end of the blood collection needle tube 51 when being slid toward a leading end side after the blood collection needle tube 51 is removed from a blood vessel is attached to the hub 54. In addition, a winged member 56 for stable fixation to skin of a living body or the like is fixed to the protector 55. Specifically, the blood collection member 5 of the present embodiment is configured as a butterfly needle (winged needle) such as a protector-attached medical needle disclosed in Japanese Patent Laid-Open No. 2017-196060 of the applicant.

The blood collection tube holder body 11 includes a protrusion part 14 protruding from a central part of a bottom part 13 toward the leading end side, and a needle base 15 attached to the protrusion part 14 by screwing. The needle base 15 includes a rubber sleeve 18 as an elastic sheath body that supports a hollow needle tube 17 having a sharp leading end protruding into a hollow part 16 of the blood collection tube holder body 11 and covers the needle tube 17 across its entire length, and also includes a hollow part 19 communicating with the needle tube 17 on the leading end side. In addition, a male connector 15a is provided at a leading end part of the needle base 15.

The blood collection tube holder body 11 also includes a plurality of tongue-shaped protrusion pieces 20 protruding from the bottom part 13 into the hollow part 16 of the blood collection tube holder body 11. In the present embodiment, the tongue-shaped protrusion pieces 20 are provided at four places at equal intervals in the circumferential direction of the bottom part 13. Note that part of the blood collection tube holder body 11 of the present embodiment other than the needle tube 17 and the rubber sleeve 18 is made of synthesis resin (polypropylene). The needle tube 17 is made of metal (stainless steel), and the rubber sleeve is made of synthetic rubber (isoprene rubber).

The blood collection tube holder body 11 can be connected to the blood collection member 5 when the male connector 15a of the needle base 15 is fitted to the female connector 53, and in this state, the flexible tube 52 and the needle tube 17 communicate with each other through the hollow part 19 of the needle base 15, and as a result, the blood collection needle tube 51 and the needle tube 17 communicate with each other. The fitting between the male connector 15a of the needle base 15 and the female connector 53 may be achieved through, for example, a lure taper. In the present embodiment, a male lure taper on the outer peripheral surface of the male connector 15a is fitted to a female lure taper on the inner peripheral surface of the female connector 53 when the male connector 15a of the needle base 15 is inserted into the female connector 53.

The outer peripheral surface of the blood collection tube holder body 11 is provided with a plurality of anti-slip ribs 11a continuous (extending) in an axial direction, and also provided with a flange 11b at an end part (base end part) on the opening side. In addition, a peripheral wall 11c protruding toward the leading end side is provided at a peripheral part of the outer surface (leading-end-side surface) of the bottom part 13 of the blood collection tube holder body 11. In the present embodiment, an axial dimension of the hollow part 16 is reduced to facilitate insertion and removal of the vacuum blood collection tube (not illustrated) with one hand, while the peripheral wall 11c is provided to extend the outer peripheral surface of the blood collection tube holder body 11 in the axial direction, thereby improving grasping easiness.

Figure 2:
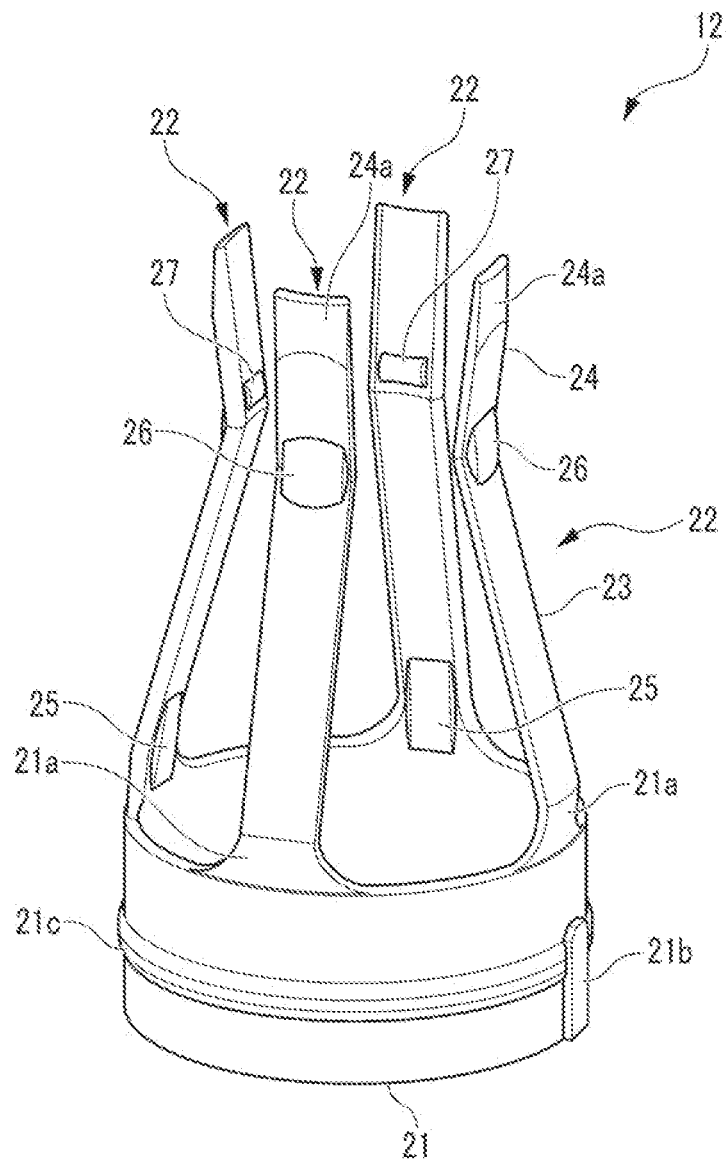
FIG. 2 is a perspective view illustrating a holding member in the exemplary configuration illustrated in FIG. 1.

The holding member 12 includes a fitting member 21 that has a hollow cylindrical shape and is internally fitted to the inner peripheral surface of the blood collection tube holder body 11, and a plurality of press-contact members 22 protruding from the fitting member 21 into the hollow part 16 of the blood collection tube holder body 11. In the present embodiment, as illustrated in FIG. 2, the press-contact members 22 are provided at four places at equal intervals in the circumferential direction of the fitting member 21, corresponding to the tongue-shaped protrusion pieces 20.

Each press-contact member 22 includes an arm-shaped part 23 protruding from the corresponding fitting member 21 toward the central axis of the hollow part 16 of the blood collection tube holder body 11, and a bend part 24 bending from a leading end part of the arm-shaped part 23 toward the inner peripheral surface of the blood collection tube holder body 11, and includes a first reinforcement piece 25 connecting the fitting member 21 and the arm-shaped part 23, and a second reinforcement piece 26 connecting the arm-shaped part 23 and the bend part 24. The press-contact member 22 includes a lock part 27 on the inward surface (inner surface) of the fitting member 21 of the bend part 24.

More specifically, the arm-shaped part 23 is a member having a band plate shape and tilted to be incrementally closer to the central axis as the member protrudes from a leading end of a trapezoid part 21a having a trapezoid plate shape and provided at four places at an end part of the fitting member 21 on the leading end side (the bottom part 13 side). The bend part 24 is a member having a band plate shape and tilted to be incrementally farther away from the central axis as the member protrudes from a leading end of the arm-shaped part 23.

The arm-shaped part 23 and the bend part 24 are each formed to have a cross-section in an arc shape and have a concave inner surface along a circumference centered at the central axis. Corners at both ends of the inner surface of each of the arm-shaped part 23 and the bend part 24 in the width direction are rounded as appropriate. In addition, a tilted surface 24a having a thickness that incrementally decreases toward a leading end is provided on the leading end side on the outer surface of the bend part 24, and corners at the leading end of the tilted surface 24a are rounded as appropriate.

The first reinforcement piece 25 is a wide rib-shaped member provided across the trapezoid part 21a and the arm-shaped part 23 on an inner surface on the valley side of a bent part between the trapezoid part 21a and the arm-shaped part 23. Similarly, the second reinforcement piece 26 is a wide rib-shaped member provided across the arm-shaped part 23 and the bend part 24 on an outer surface on the valley side of a bent part between the arm-shaped part 23 and the bend part 24. The lock part 27 is a semi-circular barrel protrusion from the inner surface of the bend part 24 on a base end side.

The outer peripheral surface of the fitting member 21 is provided with rib-shaped positioning protrusions 21b continuous (extending) in the axial direction at two places in the circumferential direction, and a ring-shaped anti-removal protrusion 21c continuous in the circumferential direction. Each positioning protrusion 21b is fitted to a recessed part provided on the inner peripheral surface of the blood collection tube holder body 11 to position the holding member 12 relative to the blood collection tube holder body 11 in the circumferential direction. The anti-removal protrusion 21c is fitted to a recessed part provided on the inner peripheral surface of the blood collection tube holder body 11 to position the holding member 12 relative to the blood collection tube holder body 11 in the axial direction and prevent the holding member 12 from falling off the blood collection tube holder body 11.

Note that, in the present embodiment, the holding member 12 is made of synthesis resin (polypropylene). The number of positioning protrusions 21b is not particularly limited but may be provided only at one place or at three or more places.

Subsequently, effects of the blood collection tube holder 1 of the present embodiment will be described below.

Figure 3:
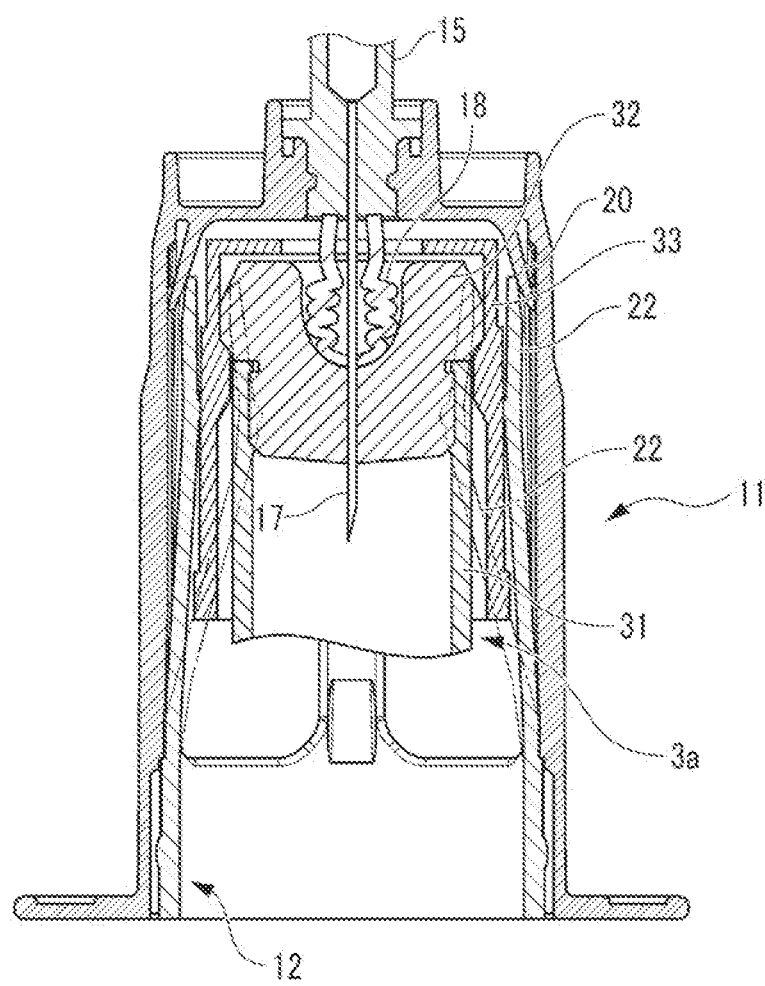
FIG. 3 is an explanatory cross-sectional view illustrating a state in which a first blood collection tube is inserted into the blood collection tube holder in the exemplary configuration illustrated in FIG. 1.

In the blood collection tube holder 1 of the present embodiment, when the male connector 15a of the needle base 15 is fitted to the female connector 53, a vacuum blood collection tube 3a is inserted on the inner periphery side of the holding member 12 internally fitted to the blood collection tube holder body 11 as illustrated in, for example, FIG. 3. The vacuum blood collection tube 3a is of an over-cap type and includes a blood collection tube body 31 as a hollow bottomed tubular body made of glass, hard plastic, or the like, a rubber cap 32 that blocks an opening end part of the blood collection tube body 31, and an outer cylindrical tube (over-cap) 33 that is made of synthesis resin as a hollow bottomed tubular body that protects the blood collection tube body 31 and the rubber cap 32. The outer cylindrical tube 33 is externally fitted to the rubber cap 32 and includes, at a bottom part, an opening part through which the rubber cap 32 is partially exposed.

When the vacuum blood collection tube 3a is inserted on the inner periphery side of the holding member 12, the press-contact members 22 protruding from the fitting member 21 into the hollow part 16 of the blood collection tube holder body 11 are pressed by the vacuum blood collection tube 3a and swing and deform from a state illustrated with virtual lines in FIG. 3 toward the inner peripheral surface of the blood collection tube holder body 11. In this state, the arm-shaped part 23 and the bend part 24 of each press-contact member 22 are substantially straight in a cross-sectional view as a result of pressing by the vacuum blood collection tube 3a and pressed to contact the outer peripheral surface of the vacuum blood collection tube 3a as returning to the original form (the state illustrated with virtual lines in FIG. 3) by elastic force of the press-contact member 22.

When the vacuum blood collection tube 3a is inserted on the inner periphery side of the holding member 12, the rubber cap 32 contacts the rubber sleeve 18 and presses the rubber sleeve 18 further toward the needle base 15. As a result, the needle tube 17 penetrates the rubber sleeve 18 and the rubber cap 32 and is inserted into the vacuum blood collection tube 3a, and the rubber sleeve 18 is compressed and folded in an accordion shape between the rubber cap 32 and the needle base 15.

When the needle tube 17 is inserted into the vacuum blood collection tube 3a, since the needle tube 17 communicates with the blood collection needle tube 51 through the hollow part 19 of the needle base 15 and the flexible tube 52, a blood specimen collected through the blood collection needle tube 51 of the blood collection member 5 is introduced into the vacuum blood collection tube 3a through the flexible tube 52 and the needle tube 17.

In this state, the rubber sleeve 18 being compressed as described above and folded in an accordion shape between the rubber cap 32 and the needle base 15 presses the vacuum blood collection tube 3a toward the opening side (the fitting member 21 side) as returning to the original form by elastic force of the rubber sleeve 18, and thus the vacuum blood collection tube 3a being held by press-contact with the press-contact members 22 potentially falls off the blood collection tube holder body 11.

However, in the blood collection tube holder 1 of the present embodiment, the arm-shaped part 23 and the bend part 24 of each press-contact member 22 are substantially straight in a cross-sectional view as a result of pressing by the vacuum blood collection tube 3a as described above, and the tongue-shaped protrusion piece 20 swings and deforms toward the inner peripheral surface of the blood collection tube holder body 11 as a leading end of the bend part 24 contacts the tongue-shaped protrusion piece 20. When swinging as described above, the tongue-shaped protrusion piece 20 presses the leading end of the bend part 24 toward the outer peripheral surface of the blood collection tube as returning to the original form by elastic force of the tongue-shaped protrusion piece 20.

As a result, press-contact of each press-contact member 22 with the outer peripheral surface of the vacuum blood collection tube 3a is assisted by pressing force of the tongue-shaped protrusion piece 20 in addition to elastic force of the press-contact member 22, and thus the vacuum blood collection tube 3a can be held with stronger force. Accordingly, it is possible to prevent the vacuum blood collection tube 3a falling off the blood collection tube holder body 11 when the vacuum blood collection tube 3a is pressed toward the opening side by the rubber sleeve 18 being compressed.

In the blood collection tube holder 1 of the present embodiment, the vacuum blood collection tube 3a is removed once a blood specimen in a predetermined amount is accumulated in the vacuum blood collection tube 3a. In this case, along with removal of the vacuum blood collection tube 3a, the rubber sleeve 18 returns to the original form and covers the needle tube 17 across its entire length, thereby preventing leakage of the blood specimen out of the needle tube 17.

Figure 4:
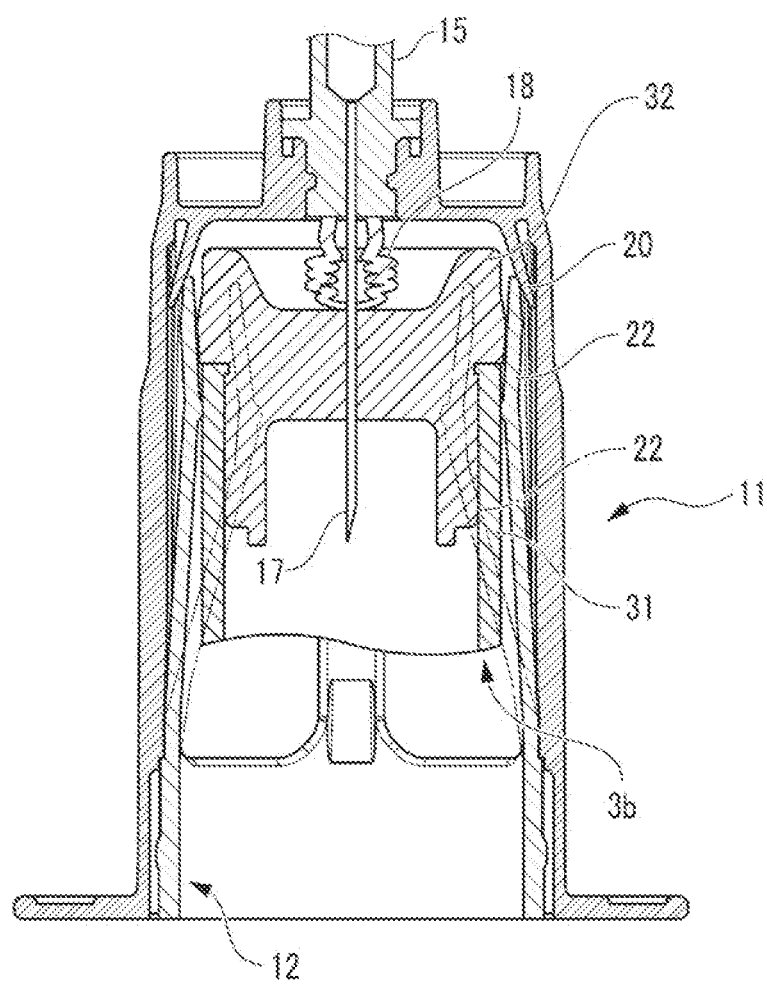
FIG. 4 is an explanatory cross-sectional view illustrating a state in which a second blood collection tube is inserted into the blood collection tube holder in the exemplary configuration illustrated in FIG. 1.

In the blood collection tube holder 1 of the present embodiment, a vacuum blood collection tube 3b may be inserted on the inner periphery side of the holding member 12 internally fitted to the blood collection tube holder body 11 as illustrated in, for example, FIG. 4 while connection to the blood collection member 5 is maintained as the male connector 15a of the needle base 15 is fitted to the female connector 53. The vacuum blood collection tube 3b is of a rubber plug cap type and includes the blood collection tube body 31 as a hollow bottomed tubular body made of glass, hard plastic, or the like, and the rubber cap 32 that blocks the opening end part of the blood collection tube body 31.

In a case of the vacuum blood collection tube 3b of a rubber plug cap type as well, similarly to a case of the vacuum blood collection tube 3a of an over-cap type, the blood collection tube holder 1 of the present embodiment can prevent the vacuum blood collection tube 3b from falling off the blood collection tube holder body 11 when the vacuum blood collection tube 3b is pressed toward the back side by the rubber sleeve 18 being compressed.

Figure 5:
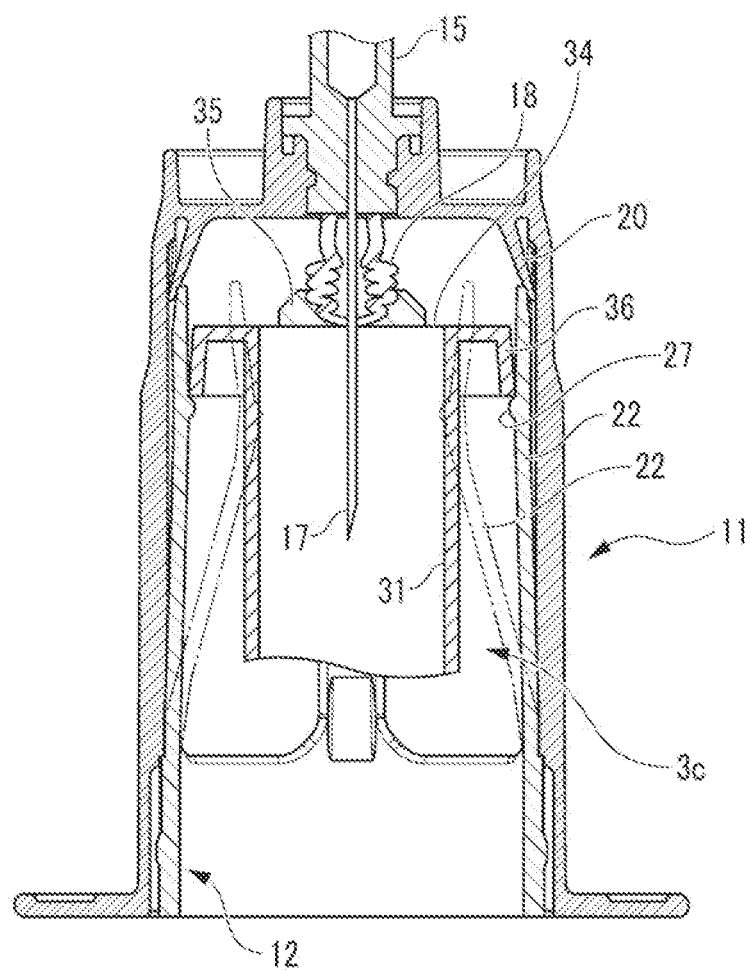
FIG. 5 is an explanatory cross-sectional view illustrating a state in which a third blood collection tube is inserted into the blood collection tube holder in the exemplary configuration illustrated in FIG. 1.

In the blood collection tube holder 1 of the present embodiment, a vacuum blood collection tube 3c may be inserted on the inner periphery side of the holding member 12 internally fitted to the blood collection tube holder body 11 as illustrated in, for example, FIG. 5 while connection to the blood collection member 5 is maintained as the male connector 15a of the needle base 15 is fitted to the female connector 53. The vacuum blood collection tube 3c is of a seal type and includes the blood collection tube body 31 as a hollow bottomed tubular body made of glass, hard plastic, or the like, and a seal member 34 that blocks the opening end part of the blood collection tube body 31. The seal member 34 includes a valve body 35 made of rubber at a central part of a sheet made of, for example, an aluminum film. The blood collection tube body 31 includes a flange part 36 extending outward from the opening end part. Note that the flange part 36 may be configured as a separate member fixed to the blood collection tube body 31.

In a case of the vacuum blood collection tube 3c of a seal type as well, similarly to cases of the vacuum blood collection tube 3a of an over-cap type and the vacuum blood collection tube 3b of a rubber plug cap type, the blood collection tube holder 1 of the present embodiment can prevent the vacuum blood collection tube 3c from falling from the blood collection tube holder body 11 when the vacuum blood collection tube 3c is pressed toward the back side by the rubber sleeve 18 being compressed. Moreover, since the vacuum blood collection tube 3c of a seal type includes the flange part 36, the flange part 36 can be locked to the lock part 27 of each bend part 24, and thus the vacuum blood collection tube 3c can be further reliably prevented from falling off the blood collection tube holder body 11.

In the present embodiment, since the blood collection tube holder body 11 is provided with the tongue-shaped protrusion pieces 20, appropriate holding force can be generated without increase in the entire thickness and size of the holding member 12. As a result, the blood collection tube holder body 11 can have a compact configuration while reliably preventing fall of the vacuum blood collection tubes 3a, 3b, and 3c, and thus insertion-removal easiness of the vacuum blood collection tube 3a and grasping easiness of the blood collection tube holder body 11 are not encumbered.

In the present embodiment, each bend part 24 contacts the corresponding tongue-shaped protrusion piece 20 after insertion of the vacuum blood collection tubes 3a, 3b, and 3c proceeds to some extent, but before that, elastic force as insertion resistance is only elastic force of the holding member 12, and thus the vacuum blood collection tubes 3a, 3b, and 3c can be easily inserted while being reliably prevented from falling.

In the present embodiment, since the first reinforcement pieces 25 and the second reinforcement pieces 26 are provided at bent parts that deform by being pressed to open along with insertion of the vacuum blood collection tubes 3a, 3b, and 3c, the holding member 12 can have a compact configuration while generating appropriate holding force. Moreover, since the lock parts 27 are provided to the holding member 12, it is possible to stably hold the vacuum blood collection tube 3c of a seal type, which is likely to be tilted relative to the blood collection tube holder body 11 due to relatively small-diameters of parts except for the flange part 36, thereby preventing falling.

In the present embodiment, since each tilted surface 24a is provided on the leading end side on the outer surface of the bend part 24 and the leading end of the tilted surface 24a is rounded, contact with the corresponding tongue-shaped protrusion piece 20 and deformation of the holding member 12 and the tongue-shaped protrusion piece 20 after the contact are smoothly performed. Moreover, since both ends of the inner surfaces of the arm-shaped part 23 and the bend part 24 in the width direction are rounded, a label or the like bonded to the outer peripheral surface of the vacuum blood collection tube 3a, 3b, or 3c is prevented being caught on the arm-shaped part 23 or the bend part 24 and flaked or damaged.

Note that each tongue-shaped protrusion piece 20 may be configured so that the leading end part thereof contacts or does not contact the inner peripheral surface of the blood collection tube holder body 11 when the tongue-shaped protrusion piece 20 swings and deforms along with insertion of the vacuum blood collection tubes 3a, 3b, and 3c. Similarly, each press-contact member 22 may be configured so that any part thereof contacts or does not contact the inner peripheral surface of the blood collection tube holder body 11 when the press-contact member 22 swings and deforms along insertion of the vacuum blood collection tubes 3a, 3b, and 3c.

The blood collection tube holder 1 may also include, on the inner peripheral surface of the blood collection tube holder body 11, for example, a rib-shaped contact part (not illustrated) that extends in the length direction (the axial direction) and contacts the outer peripheral surface of the vacuum blood collection tube 3a, 3b, or 3c. Alternatively, the blood collection tube holder 1 may include, on the inner peripheral surface of the blood collection tube holder body 11, for example, a groove-shaped recessed part (not illustrated) that extends in the length direction and in which each swinging and deforming press-contact member 22 is housed (to avoid interference).

When the above-described contact part is provided, the vacuum blood collection tubes 3a, 3b, and 3c can be prevented from being tilted relative to the blood collection tube holder body 11 so that the needle tube 17 appropriately penetrates the vacuum blood collection tubes 3a, 3b, and 3c, and the vacuum blood collection tubes 3a, 3b, and 3c can be stably held. When the above-described recessed part is provided, it is possible to reduce the outer diameter of the blood collection tube holder body 11 to improve grasping easiness and operating easiness while enabling reliable holding of the vacuum blood collection tubes 3a, 3b, and 3c due to provision of the holding member 12. Note that, when the above-described recessed part is provided, as well, it may be configured that each swinging and deforming tongue-shaped protrusion piece 20 or press-contact member 22 contacts or does not contact the bottom surface of the recessed part.

The number of press-contact members 22 and the number of tongue-shaped protrusion pieces 20 are not particularly limited but may be optional. Each tongue-shaped protrusion piece 20 may protrude from the inner peripheral surface of the blood collection tube holder body 11 or may be configured as a separate member fixed to the blood collection tube holder body 11. The first reinforcement pieces 25, the second reinforcement pieces 26, or the lock parts 27 may be omitted from the holding member 12 when sufficient holding force can be obtained with the tongue-shaped protrusion pieces 20.

The needle base 15 may be integrally formed with the protrusion part 14. The male connector 15a may be provided to the protrusion part 14 separately from the needle base 15. The male connector 15a may be include a lock member provided with a female screw. Instead of the male connector 15a, a blood collection needle tube with which a blood vessel is pierced may be provided to the needle base 15.

In the blood collection kit 2, the blood collection member 5 may be other than a butterfly needle and may be connected to the blood collection tube holder body 11 not through the flexible tube 52. Moreover, the blood collection member 5 may include no flexible tube 52 and may be connected to the blood collection tube holder body 11 through an extension tube including an appropriate connector.

The material of part of the blood collection tube holder body 11 except for the needle tube 17 and the rubber sleeve 18 may be, in place of polypropylene, for example, polycarbonate, polystyrene, acrylic nitrile butadiene styrene (ABS resin), polyethylene terephthalate, polyvinyl chloride, or methyl polymethacrylate resin (acrylic resin), and this is same for the holding member 12. The material of the rubber sleeve 18 may be, in place of isoprene rubber, for example, silicone rubber, butadiene rubber, butyl rubber, natural rubber, urethane rubber, or fluoro-rubber.

Subsequently, another exemplary configuration of the blood collection tube holder 1 and the blood collection kit 2 will be described below. Note that, in the following description, any component same as that illustrated in FIGS. 1 to 5 is denoted by the same reference sign, and detailed description thereof is omitted.

Figure 6:
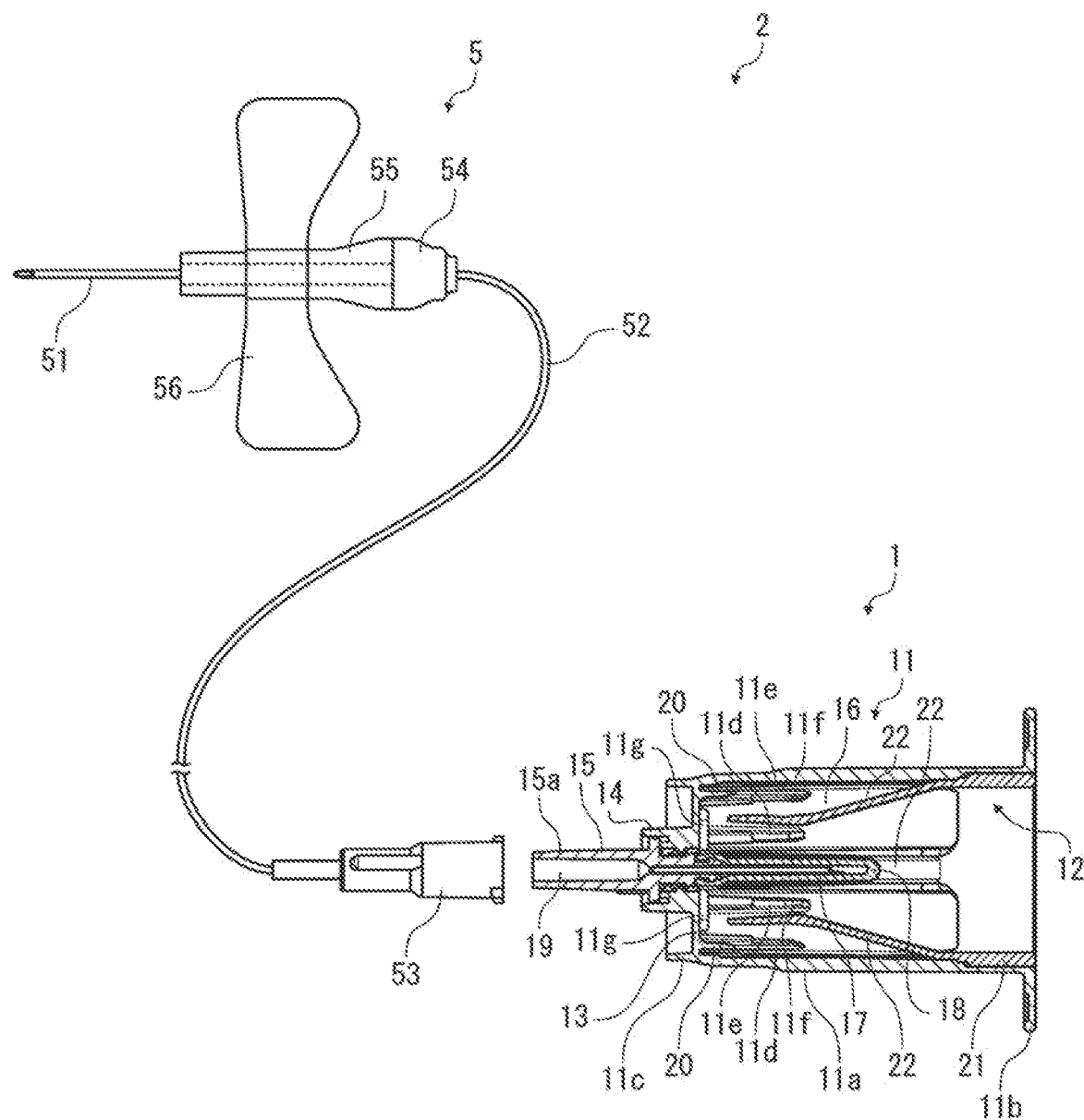
FIG. 6 is an explanatory diagram illustrating another exemplary configuration of the blood collection tube holder and the blood collection kit of the present invention.

FIG. 6 illustrates an example in which a first contact part 11d and a second contact part 11e that contact the outer peripheral surface of the flange part 36 of the vacuum blood collection tube 3c are provided on the inner peripheral surface of the blood collection tube holder body 11 and a lock part 11f is provided the second contact part 11e in place of the lock part 27 provided to each press-contact member 22. As illustrated in FIG. 6, similarly to the example illustrated in FIG. 1, the blood collection tube holder 1 of this example is part of the configuration of the blood collection kit 2 including the blood collection member 5.

Figure 7:
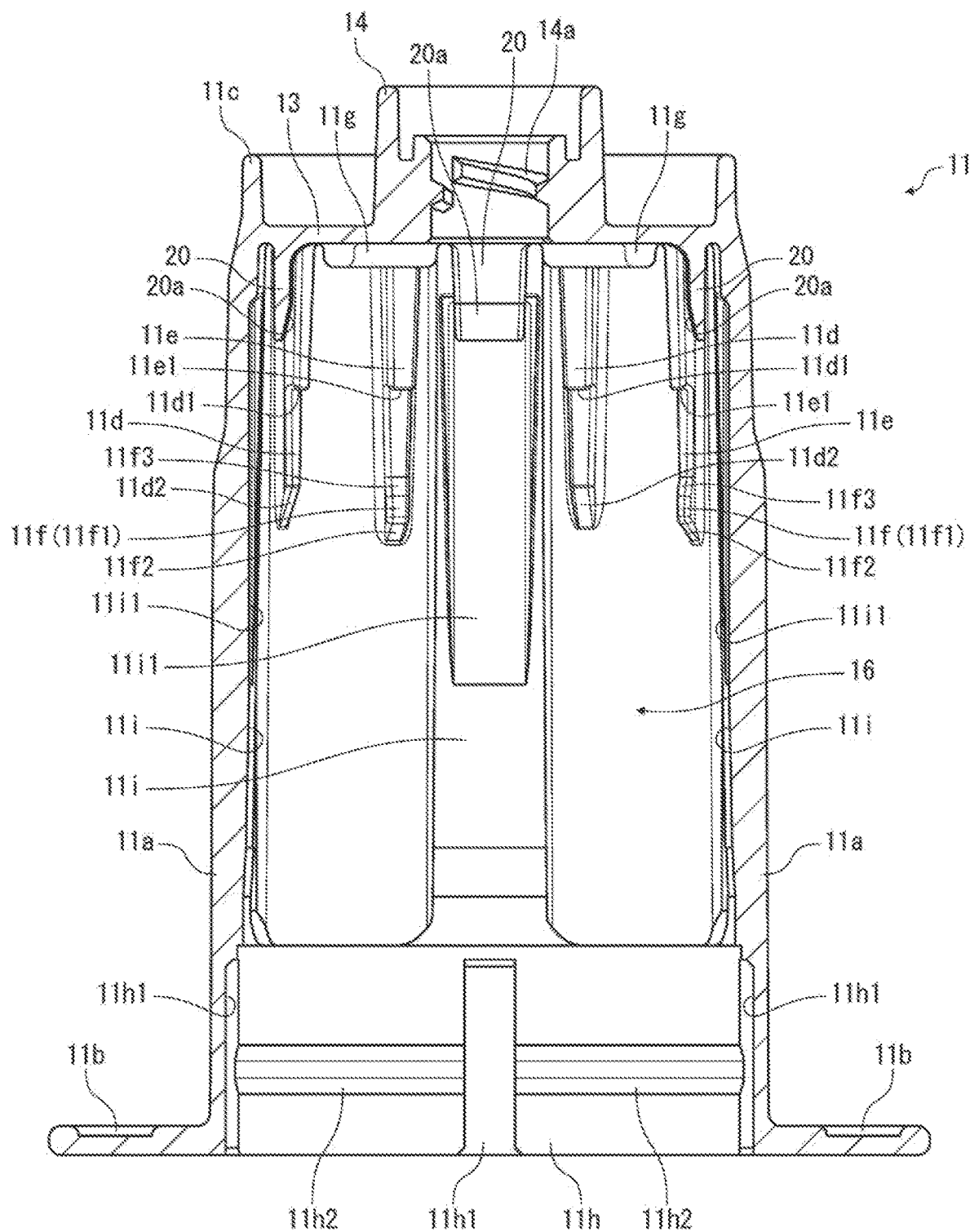
FIG. 7 is an explanatory cross-sectional view illustrating a blood collection tube holder body in the exemplary configuration illustrated in FIG. 6.

FIG. 7 is an explanatory cross-sectional view of the blood collection tube holder body 11 in the example illustrated in FIG. 6. Note that illustration of the needle base 15, the needle tube 17, and the rubber sleeve 18 is omitted in FIG. 7. As illustrated in FIG. 7, the first contact part 11d and the second contact part 11e protrude toward the central axis on the inner peripheral surface of the blood collection tube holder body 11 are formed in a rib shape continuous (extending) in the axial direction from the bottom part 13 toward the opening side. The first contact parts 11d and the second contact parts 11e are disposed at four places of the blood collection tube holder body 11 in the circumferential direction and alternately arranged in the circumferential direction.

Each first contact part 11d is formed in a stepped shape in which the amount of protrusion is larger on the bottom part 13 side, and includes a stepped part 11d1 at a middle part. In addition, a tilt part 11d2 in which the amount of protrusion incrementally decreases toward the opening side and that is connected to the inner peripheral surface is provided at an end part of the first contact part 11d on the opening side. Similarly, each second contact part 11e is formed in a stepped shape in which the amount of protrusion is larger on the bottom part 13 side, and includes a stepped part 11e1 at a middle part. In addition, the lock part 11f that locks to the flange part 36 of the vacuum blood collection tube 3c is provided at an end part of the second contact part 11e on the opening side.

The lengths of each first contact part 11d and each second contact part 11e in the axial direction are not particularly limited but are set to be about ⅓ of the length of the hollow part 16 of the blood collection tube holder body 11 in the axial direction in this example.

In this example, third contact parts 11g that position the vacuum blood collection tube 3a or 3b in the axial direction when contacting a leading surface of the vacuum blood collection tube 3a or 3b are provided at four places on the inner surface of the bottom part 13. The third contact parts 11g are formed as four arc-shaped protrusions toward the opening side, which are centered at the central axis of the hollow part 16 when viewed from the opening side. When such third contact parts 11g are provided, the vacuum blood collection tube 3a or 3b can be disposed at an appropriate position in the axial direction and prevented from being tilted after the needle tube 17 penetrates.

Furthermore, in this example, the inner peripheral surface of the blood collection tube holder body 11 is provided with a first recessed part 11h in which a part other than the trapezoid parts 21a of the fitting member 21 of the holding member 12 is housed, and a second recessed part 11i in which the corresponding trapezoid part 21a of the fitting member 21 is housed and at least part of the corresponding press-contact member 22 and the corresponding swinging tongue-shaped protrusion piece 20 is housed (to avoid interference). As described above, when the first recessed part 11h and the second recessed part 11i are provided, the outer diameter of the blood collection tube holder body 11 can be reduced to improve grasping easiness and operating easiness. Moreover, when the first recessed part 11h or the second recessed part 11i is provided, the freedom of designing the thickness and shape of the holding member 12 increases, and thus elastic force of each press-contact member 22 can be increased as compared to conventional cases, thereby generating sufficient holding force.

The first recessed part 11h is formed in a groove shape continuous (extending) in the circumferential direction at an end part of the inner peripheral surface of the blood collection tube holder body 11 on the opening side. A positioning recessed part 11h1 in which the corresponding positioning protrusion 21b of the holding member 12 is housed and an anti-removal recessed part 11h2 in which the anti-removal protrusion 21c of the holding member 12 is housed are provided at corresponding positions on a bottom surface of the first recessed part 11h.

Each second recessed part 11i is formed in a groove shape extending in the axial direction from the corresponding first recessed part 11h toward the bottom part 13 side at a position corresponding to the corresponding press-contact member 22 on the inner peripheral surface of the blood collection tube holder body 11. When each second recessed part 11i is formed in this manner, the freedom of designing each arm-shaped part 23 to which large moment is applied at swinging along with insertion of the vacuum blood collection tube 3a, 3b, or 3c and designing the fitting member 21 supporting the arm-shaped part 23 further increases, and thus fall of the vacuum blood collection tube 3a, 3b, or 3c can be more reliably prevented with larger elastic force of the press-contact members 22. In addition, an additional recessed part 11i1 having a depth increased in accordance with the corresponding tongue-shaped protrusion piece 20 is provided on the bottom part 13 side on a bottom surface of the corresponding second recessed part 11i.

The depths of each first recessed part 11h and each second recessed part 11i are not particularly limited, but are preferably such depths that a step generated between the inner peripheral surface of the blood collection tube holder body 11 and the inner peripheral surface of the fitting member 21 is small, more preferably such depths that the inner peripheral surface and the inner peripheral surface of the fitting member 21 are flush.

When the inner peripheral surface of the blood collection tube holder body 11 and the inner peripheral surface of the fitting member 21 are flush, it is possible to prevent a label bonded to the outer peripheral surface of the vacuum blood collection tube 3a, 3b, or 3c or the seal member 34 of the vacuum blood collection tube 3c of a seal type from being caught on the step and flaked or damaged at insertion or removal of the vacuum blood collection tube.

Note that only the first recessed parts 11h or the second recessed parts 11i may be provided. Moreover, only the positioning recessed part 11h1 or the anti-removal recessed part 11h2 may be provided as the first recessed part 11h. Furthermore, the additional recessed parts 11i1 may be omitted from the second recessed parts 11i.

Additionally, in this example, a tilted surface 20a having a thickness that incrementally decreases toward a tip of the tongue-shaped protrusion piece 20 is provided on the tip side of the inner surface of the tongue-shaped protrusion piece 20 and a corner at a leading end of the tilted surface 20a is rounded as appropriate so that contact with the holding member 12 and deformation of the holding member 12 and the tongue-shaped protrusion piece 20 after the contact are more smoothly performed.

A two-thread female screw 14a that is screwed with a male screw of the needle base 15 is provided at the protrusion part 14 of the blood collection tube holder body 11, and in this example, the two threads are provided not to overlap with each other in the axial direction, which allows simplification of the structure of a resin-shaping mold.

Figure 8:
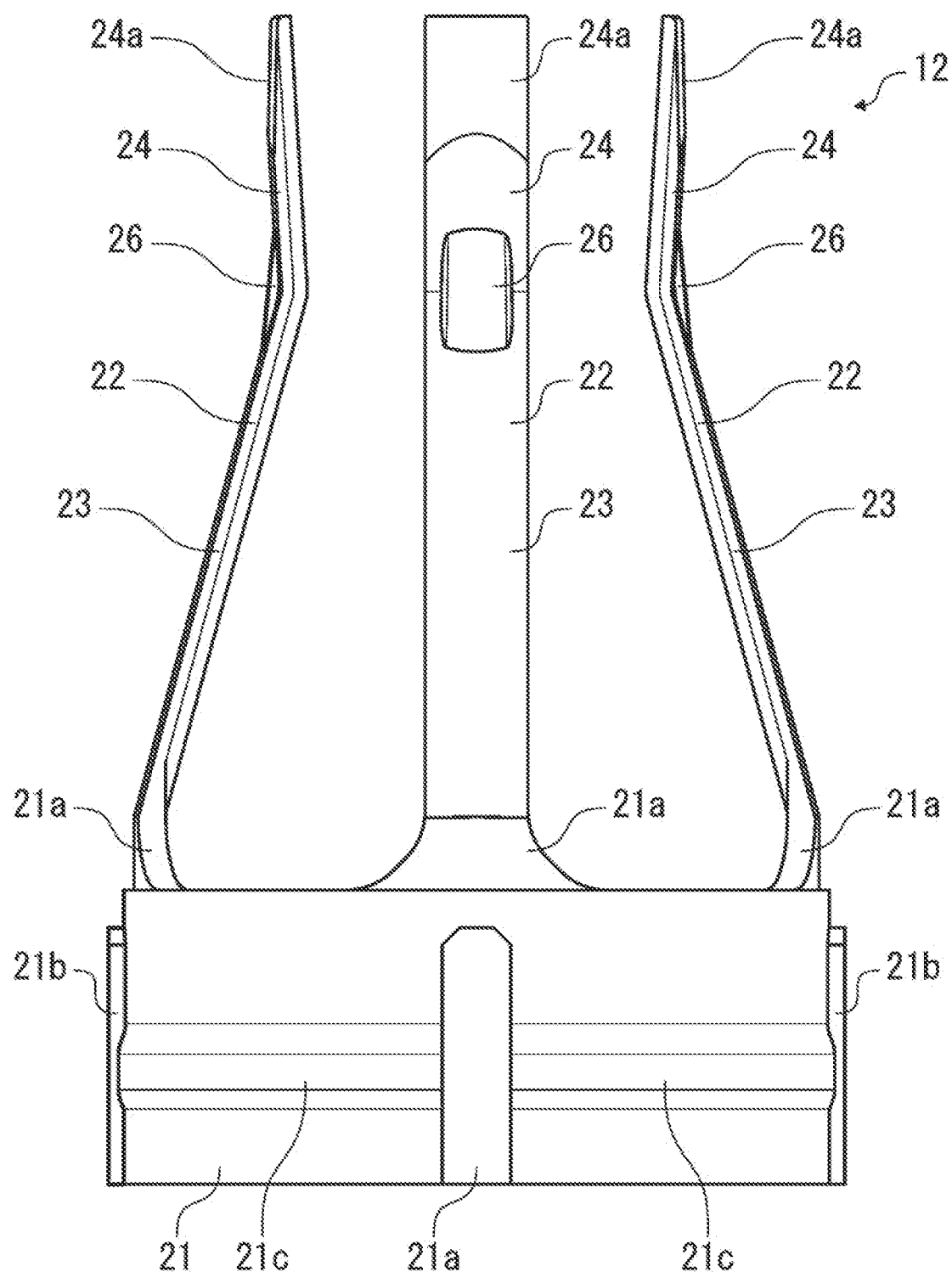
FIG. 8 is an explanatory cross-sectional view illustrating the holding member in the exemplary configuration illustrated in FIG. 6.

FIG. 8 is an exterior diagram of the holding member 12 in the example illustrated in FIG. 6. As described above, the lock parts 27 are omitted in this example. In addition, the positioning protrusions 21b are provided at four places in the circumferential direction in this example, which facilitates assembly of the holding member 12 to the blood collection tube holder body 11. Moreover, in this example, the first reinforcement pieces 25 are omitted to reduce the insertion resistance at start of insertion of the vacuum blood collection tube 3a, 3b, or 3c while appropriate holding force is maintained with the second reinforcement pieces 26.

Thus, only the first reinforcement pieces 25 or the second reinforcement pieces 26 may be provided, and in this manner, holding force by the holding member 12 can be adjusted as appropriate. Note that the first reinforcement pieces 25 and the second reinforcement pieces 26 may be provided in different manners among the press-contact members 22 or the first reinforcement pieces 25 and the second reinforcement pieces 26 may be both omitted.

Figure 9A:
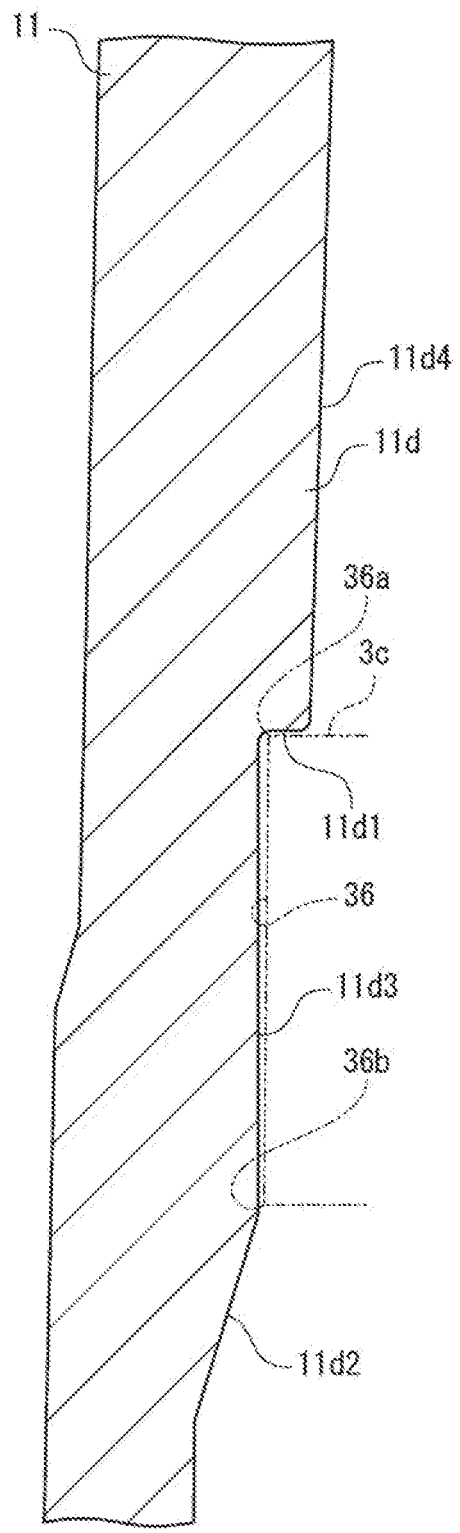
FIG. 9A is an enlarged explanatory cross-sectional view illustrating a first contact part in the exemplary configuration illustrated in FIG. 6.
Figure 9B:
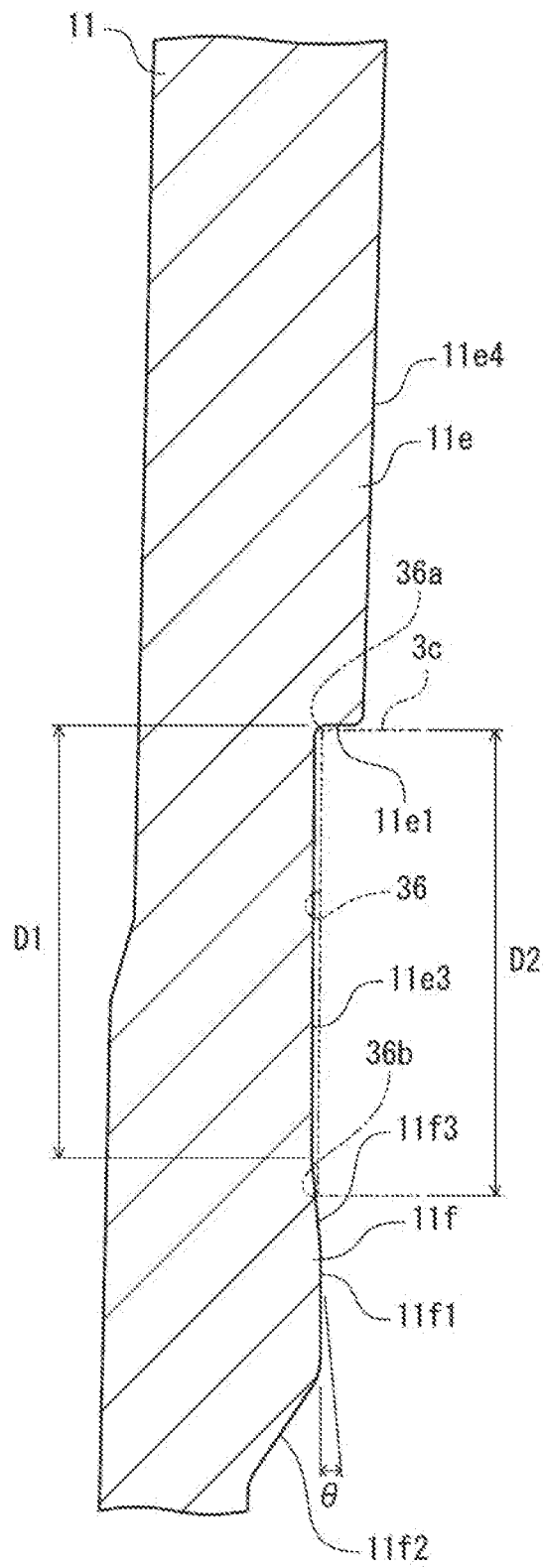
FIG. 9B is an enlarged explanatory cross-sectional view illustrating a second contact part in the exemplary configuration illustrated in FIG. 6.

FIG. 9A is an enlarged explanatory cross-sectional view illustrating each first contact part 11d, and FIG. 9B is an enlarged explanatory cross-sectional view illustrating each second contact part 11e. As illustrated with virtual lines in FIG. 9A, the vacuum blood collection tube 3c is positioned in the axial direction when a leading surface of the flange part 36 contacts the stepped part 11d1. In addition, the vacuum blood collection tube 3c is positioned in the radial direction and prevented from being tilted relative to the blood collection tube holder body 11 when the outer peripheral surface of the flange part 36 contacts a top surface 11d3 that is lower on the opening side. When being tilted at insertion, the vacuum blood collection tube 3c is guided by the tilt part 11d2 to a state in which the outer peripheral surface of the flange part 36 contacts the top surface 11d3.

Similarly at the second contact part 11e, as illustrated with virtual lines in FIG. 9B, the vacuum blood collection tube 3c is positioned in the axial direction when the leading surface of the flange part 36 contacts the stepped part 11e1, and is positioned in the radial direction and prevented from being tilted relative to the blood collection tube holder body 11 when the outer peripheral surface of the flange part 36 contacts a top surface 11e3 that is lower on the opening side.

In addition, the vacuum blood collection tube 3c is prevented from falling when the lock parts 11f are locked to the flange part 36.

In this example, each lock part 11f is provided to further protrude from the top surface 11e3. The lock part 11f is formed in a trapezoid shape having a parallel surface 11f1 provided at a top part in substantially parallel to the central axis, an opening-side tilted surface 11f2, the amount of protrusion of which incrementally decreases toward the opening side on the opening side of the parallel surface 11f1, and a bottom-part-side tilted surface 11f3, the amount of protrusion of which incrementally decreases toward the bottom part 13 side on the bottom part 13 side of the parallel surface 11f1. Note that the opening-side tilted surface 11f2 is provided in connection with the inner peripheral surface and has a function same as that of the tilt part 11d2 of the first contact part 11d.

At insertion of the vacuum blood collection tube 3c, the blood collection tube holder body 11 and the flange part 36 need to be elastically deformed so that the flange part 36 moves over the lock part 11f. Thus, the insertion resistance increases when a corner 36a of the flange part 36 on the leading end side (the bottom part 13 side) is in contact with the opening-side tilted surface 11f2, and decreases when a corner 36b of the flange part 36 on the base end side (the opening side) is in contact with the bottom-part-side tilted surface 11f3. A user perceives, as a click feeling, the decrease of the insertion resistance after the increase, and can understand, only with sensing at a finger, that the vacuum blood collection tube 3c is disposed at an appropriate position.

In this example, a parallel surface 11f1 is provided between the opening-side tilted surface 11f2 and the bottom-part-side tilted surface 11f3 to appropriately generate the click feeling. Specifically, when the parallel surface 11f1 is not provided, the flange part 36 is sandwiched at a corner between the opening-side tilted surface 11f2 and the bottom-part-side tilted surface 11f3 of each of the four lock parts 11f after the corner 36a of the flange part 36 on the leading end side moves over the opening-side tilted surface 11f2, and thus the vacuum blood collection tube 3c is likely to be tilted relative to the blood collection tube holder body 11. When the vacuum blood collection tube 3c is tilted relative to the blood collection tube holder body 11, the corner 36b of the flange part 36 on the base end side contacts the bottom-part-side tilted surface 11f3 at timings different among the four lock parts 11f in some cases, and in such a case, click feelings are continuously generated and thus the user potentially cannot understand appropriate disposition of the vacuum blood collection tube 3c.

However, when the parallel surface 11f1 is provided between the opening-side tilted surface 11f2 and the bottom-part-side tilted surface 11f3, the vacuum blood collection tube 3c can be prevented from being tilted after the corner 36a of the flange part 36 on the leading end side moves over the opening-side tilted surface 11f2, and thus the corner 36b of the flange part 36 on the base end side can be made contact with the bottom-part-side tilted surfaces 11f3 of the four lock parts 11f at substantially same timings, thereby generating an appropriate click feeling.

Moreover, in this example, a distance D1 between the stepped part 11e1 and an edge (boundary with the top surface 11e3) of the bottom-part-side tilted surface 11f3 on the bottom part 13 side is set to be smaller than an axial dimension D2 of the flange part 36 (in other words, the bottom-part-side tilted surface 11f3 is provided to protrude beyond the top surface 11e3 at a position separated from the stepped part 11e1 by the distance D2) so that a tilt angle θ of the bottom-part-side tilted surface 11f3 with respect to the central axis can be set to be small at 5° approximately. When the distance D1 is set to be smaller than the axial dimension D2 of the flange part 36, the flange part 36 can be sandwiched between the stepped part 11e1 and the bottom-part-side tilted surface 11f3 to increase pressing force of the bottom-part-side tilted surface 11f3 on the flange part 36, and thus the vacuum blood collection tube 3c can be reliably prevented from falling when the tilt angle θ is set to be small.

When the tilt angle θ is set to be small, resistance at removal of the vacuum blood collection tube 3c from the blood collection tube holder 1 can be reduced. Accordingly, with the lock part 11f of this example, it is possible to achieve both fall prevention and removal easiness of the vacuum blood collection tube 3c.

Note that the shape of the lock part 11f is not limited to such a trapezoid shape but may be any other appropriate shape such as a pyramid shape, a dome shape, or a rectangular column shape. For example, when a click feeling is not important, the lock part 11f may be formed in a shape not including the parallel surface 11f1. The opening-side tilted surface 11f2 and the bottom-part-side tilted surface 11f3 may be curved surfaces. It is needless to say that the tilt angles of the opening-side tilted surface 11f2 and the bottom-part-side tilted surface 11f3 are not particularly limited.

In this manner, when the first contact parts 11d and the second contact parts 11e are provided on the inner peripheral surface of the blood collection tube holder body 11 and the lock parts 11f are provided at the second contact parts 11e, as well, the vacuum blood collection tube 3c of a seal type can be stably held and prevented from falling. In this case as well, it is needless to say that the vacuum blood collection tube 3a of an over-cap type and the vacuum blood collection tube 3b of a rubber plug cap type can be held and prevented from falling as in the example illustrated in FIG. 1.

Note that the number of first contact parts 11d and the number of second contact parts 11e are not particularly limited but may be optional. Only the second contact parts 11e may be provided on the inner peripheral surface of the blood collection tube holder body 11, or only the first contact parts 11d may be provided on the inner peripheral surface of the blood collection tube holder body 11 and the lock parts 27 may be provided to the press-contact members 22. Alternatively, the first contact parts 11d and the second contact parts 11e may be configured so that top surfaces 11d4 and 11e4 that are higher contact the outer peripheral surface of the vacuum blood collection tube 3a or 3b. The lock parts 11f may be provided separately from the second contact parts 11e on the inner peripheral surface of the blood collection tube holder body 11.

Figure 10:
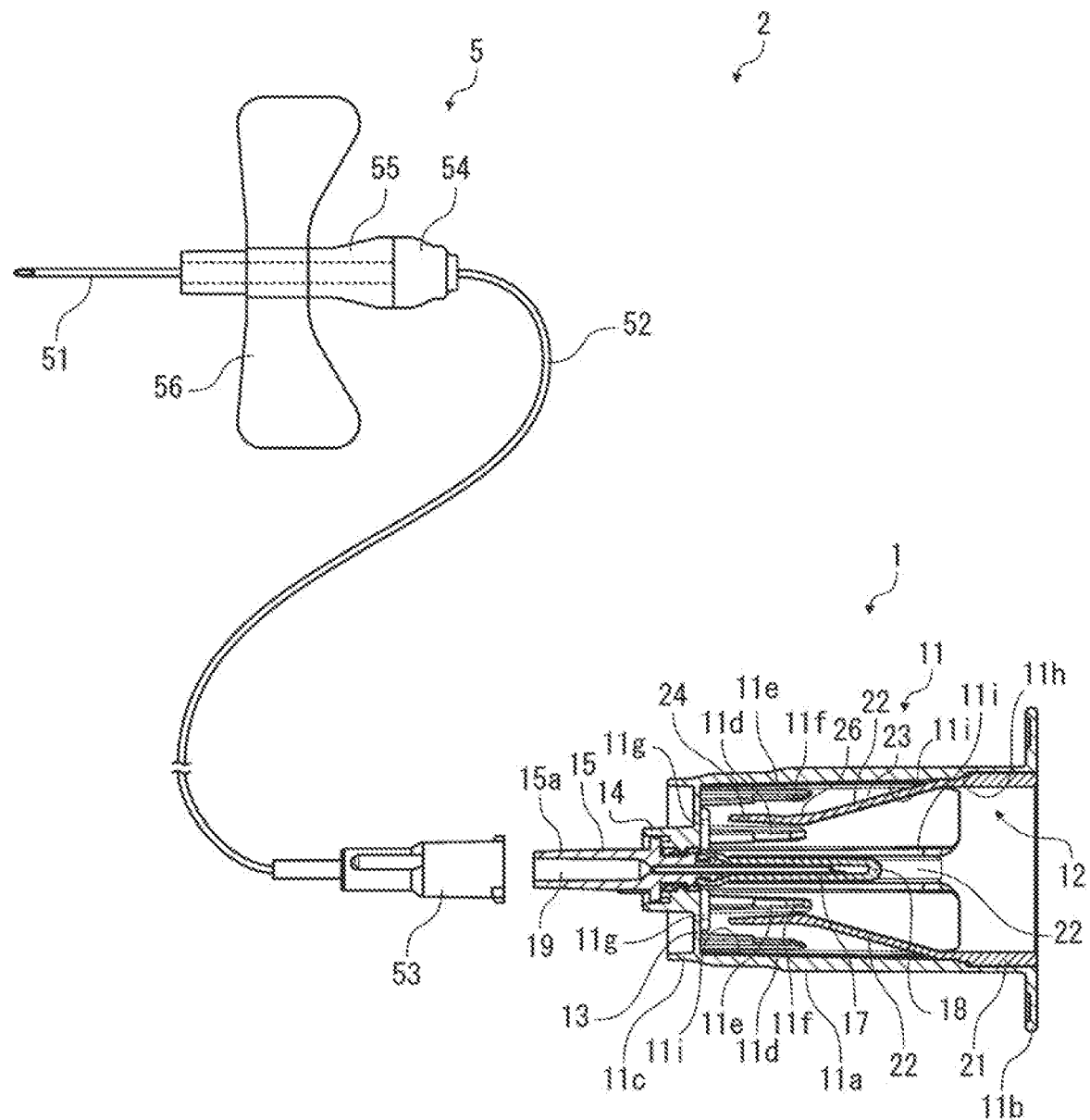
FIG. 10 is an explanatory diagram illustrating another exemplary configuration of the blood collection tube holder and the blood collection kit of the present invention.

FIG. 10 is a diagram illustrating an example in which the tongue-shaped protrusion pieces 20 are omitted in the example illustrated in FIG. 6. In this example, the additional recessed parts 11i1 of the second recessed parts 11i are omitted together with the tongue-shaped protrusion pieces 20. The dimension and shape of each second reinforcement piece 26 is adjusted as appropriate, and a leading end part of each bend part 24 is made contact with the bottom surface of the corresponding second recessed part 11i when the press-contact member 22 swings and deforms along with insertion of the vacuum blood collection tube 3a, 3b, or 3c, thereby obtaining sufficient holding force. In this manner, the tongue-shaped protrusion pieces 20 may be omitted when sufficient holding force can be obtained only with the holding member 12.

Note that, instead of making the leading end part of each bend part 24 contact with the bottom surface of the corresponding second recessed part 11*i*, the first reinforcement pieces 25 may be added to the press-contact members 22, thereby obtaining sufficient holding force. Each second recessed part 11*i* may be configured so that the leading end part of each bend part 24 contacts a part other than the corresponding second recessed part 11*i* on the inner peripheral surface of the blood collection tube holder body 11. The lock parts 11*f* may be provided separately from the second contact parts 11*e* on the inner peripheral surface of the blood collection tube holder body 11 or may be provided to the press-contact members 22. Although not illustrated, the tongue-shaped protrusion pieces 20 may be omitted in the example illustrated in FIG. 1.

Figure 11:
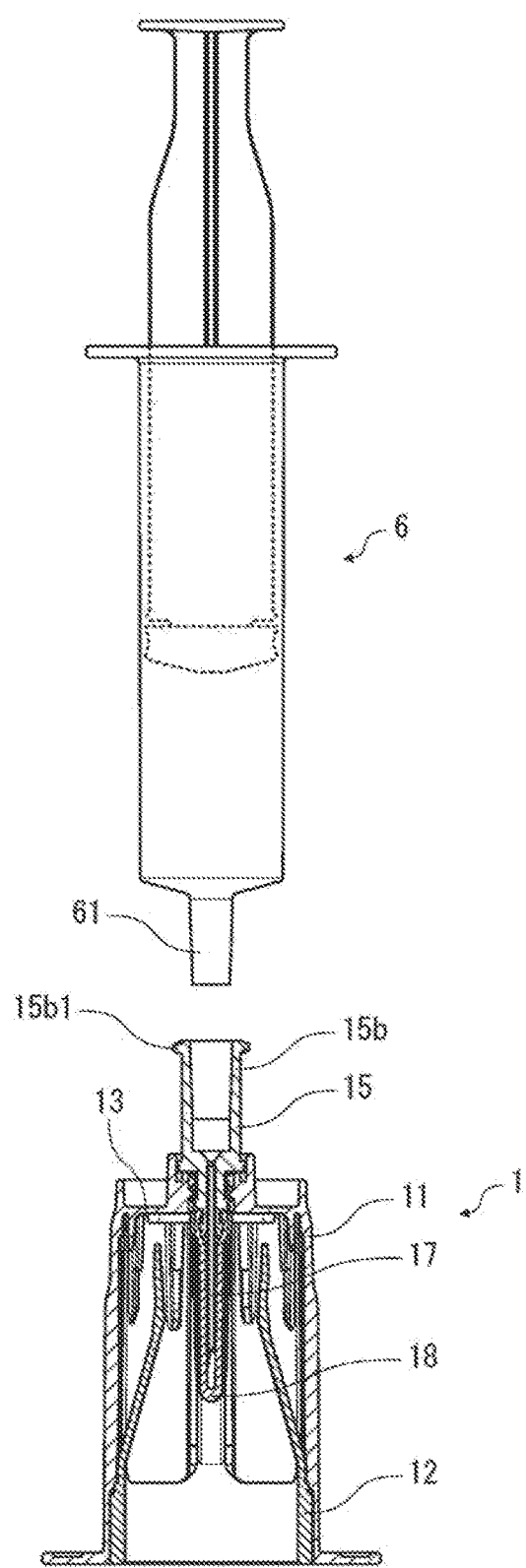
FIG. 11 is an explanatory diagram illustrating another exemplary configuration of the blood collection tube holder of the present invention.

FIG. 11 illustrates an example in which a female connector 15*b* is provided at the leading end part of the needle base 15 in place of the male connector 15*a*. As illustrated in FIG. 11, a syringe 6 used for blood collection typically includes, at a leading end, a male connector 61 for connecting a needle base (not illustrated) of a blood collection needle tube, and thus, when the female connector 15*b* is provided at the needle base 15 in this manner, the male connector 61 of the syringe 6 can be directly connected to the blood collection tube holder 1.

Thus, with the blood collection tube holder 1 illustrated in FIG. 11, a blood specimen collected in the syringe 6 can be safely dispensed to the vacuum blood collection tube 3*a*, 3*b*, or 3*c*. When the vacuum blood collection tube 3*a*, 3*b*, or 3*c* is penetrated with a blood collection needle tube connected to the syringe 6 and dispensing is performed, the blood collection needle tube connected to the syringe 6 accidentally gets stuck in, for example, a finger of the user, but such a risk of needle sticking can be reduced by using the blood collection tube holder 1 illustrated in FIG. 11.

Note that the female connector 15*b* may be provided at the protrusion part 14 separately from the needle base 15. In the example illustrated in FIG. 11, a male screw 15*b*1 is provided on the outer periphery of the female connector 15*b*, but the male screw 15*b*1 may be omitted. It is needless to say that the female connector 15*b* may be provided to any of the blood collection tube holder 1 illustrated in FIG. 1 and the blood collection tube holder 1 illustrated in FIG. 6.

Figure 12:
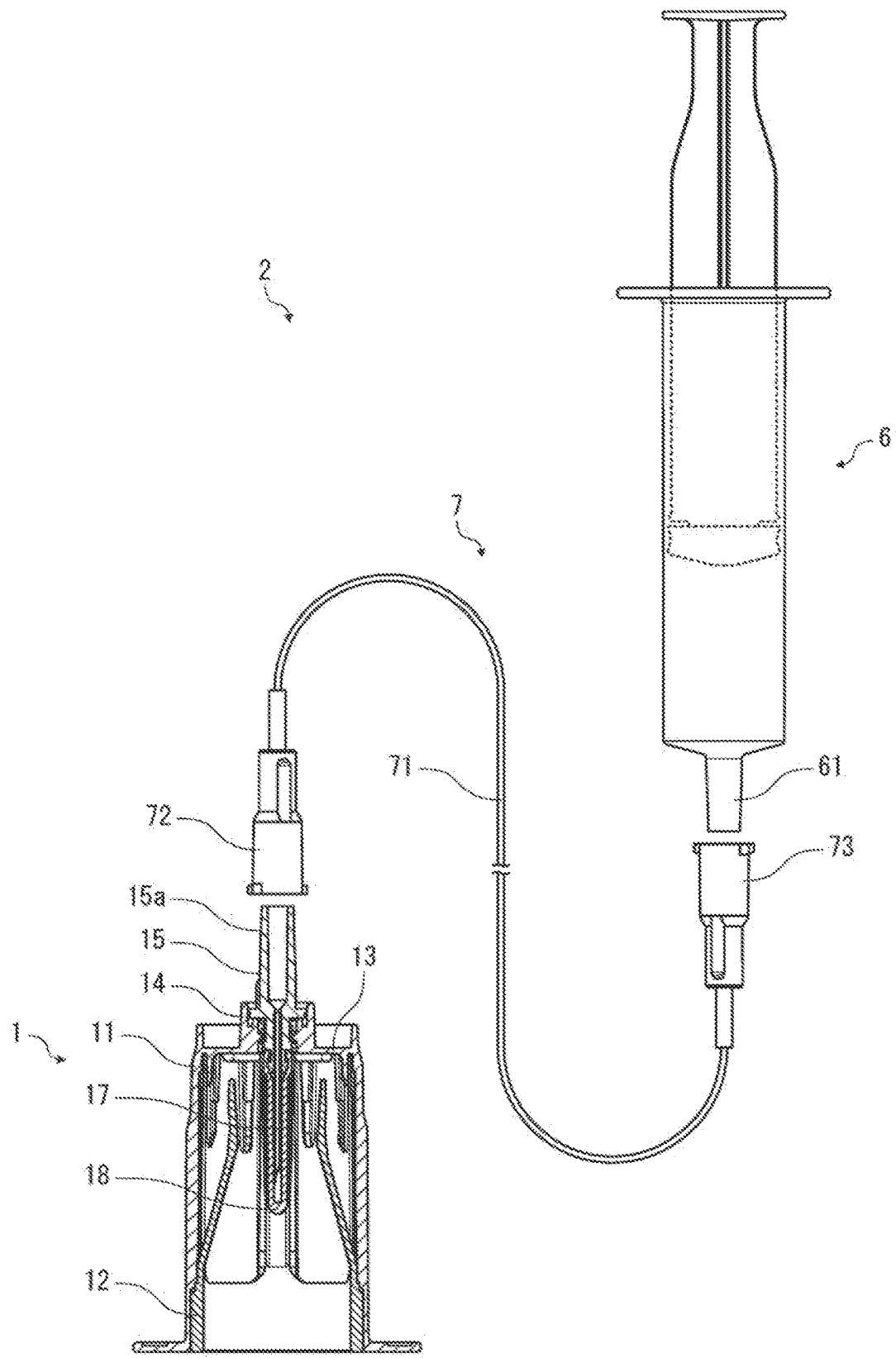
FIG. 12 is an explanatory diagram illustrating another exemplary configuration of the blood collection kit of the present invention.

FIG. 12 illustrates an example in which the blood collection kit 2 includes a connection member 7 in place of the blood collection member 5. The connection member 7 of this example includes a flexible tube 71 of a predetermined length, a female connector 72 (holder-side connector of the present invention) provided at one end of the flexible tube 71, and a female connector 73 (syringe-side connector of the present invention) provided at the other end.

With the blood collection kit 2 illustrated in FIG. 12, the syringe 6 can be connected to the blood collection tube holder 1 through the connection member 7 by connecting the female connector 72 to the male connector 15*a* of the blood collection tube holder 1 and connecting the female connector 73 to the male connector 61 of the syringe 6, and thus, similarly to the blood collection tube holder 1 illustrated in FIG. 11, a blood specimen collected in the syringe 6 can be safely dispensed to the vacuum blood collection tube 3*a*, 3*b*, or 3*c*. Moreover, with the blood collection kit 2 illustrated in FIG. 12, the connection member 7 increases the freedom of relative positions of the blood collection tube holder 1 and the syringe 6, and thus dispensing can be more easily and safely performed.

Note that the length of the flexible tube 71 is not particularly limited but is preferably 10 to 300 mm. The connection member 7 may include a hard tube, a pipe, or the like in place of the flexible tube 71 or may be configured as one member provided with the female connectors 72 and 73 at both ends.

It is needless to say that the blood collection kit 2 illustrated in FIG. 12 may include any of the blood collection tube holder 1 illustrated in FIG. 1 and the blood collection tube holder 1 illustrated in FIG. 6, and the connection member 7. Alternatively, the blood collection kit 2 may include the blood collection tube holder 1 including the female connector 15*b* illustrated in FIG. 11, and the connection member 7 provided with a male connector connectable to the female connector 15*b* at one end of the flexible tube 71 and the female connector 73 at the other end of the flexible tube 71.

Although the embodiment of the present invention is described above, the blood collection tube holder and the blood collection kit of the present invention is not limited to the above-described embodiment but may be modified in various manners without departing from the scope of the present invention.

For example, the shape and disposition of each component of the blood collection tube holder 1, the blood collection member 5, and the connection member 7 are not limited to those described above in the embodiment but may be any other appropriate shape and disposition. Furthermore, the material of each component of the blood collection tube holder 1, the blood collection member 5, and the connection member 7 is not particularly limited but may be any other appropriate material.

Effects described above in the embodiment are merely most preferable effects that can be obtained from the present invention, and the effects of the present invention are not limited to the above-described effects.

REFERENCE SIGNS LIST

1 . . . blood collection tube holder, 2 . . . blood collection kit, 3*a*, 3*b*, 3*c* . . . vacuum blood collection tube, 5 . . . blood collection member, 6 . . . syringe, 7 . . . connection member, 11 . . . blood collection tube holder body, 11*d* . . . first contact part, 11*e* . . . second contact part, 11*f*, 27 . . . lock part, 11*h* . . . first recessed part, 11*i* . . . second recessed part, 12 . . . holding member, 13 . . . bottom part, 15 . . . needle base, 15*b*, 53, 72 . . . female connector, 16 . . . hollow part, 17 . . . needle tube, 18 . . . rubber sleeve, 20 . . . tongue-shaped protrusion piece, 21 . . . fitting member, 22 . . . press-contact member, 23 . . . arm-shaped part, 24 bend part, 25 . . . first reinforcement piece, 26 . . . second reinforcement piece, 36 . . . flange part, 51 . . . blood collection needle tube.

The invention claimed is:

1. A blood collection tube holder comprising:
a blood collection tube holder body having a hollow bottomed tubular shape, a hollow part, a bottom part, an inner peripheral surface, an outer peripheral surface, a needle base, a hollow needle tube and an elastic sheath body; and
a holding member internally fitted to the inner peripheral surface and configured to detachably hold a blood collection tube in the hollow part,
the needle base provided at the bottom part, the hollow needle tube having a length, supported by the needle base and protruding into the hollow part, and the elastic sheath body covering the hollow needle tube across the length of the hollow needle tube, and wherein the holding member is internally fitted to the inner peripheral surface and includes a fitting member having a hollow tubular shape, and a plurality of press-contact members protruding from the fitting member into the hollow part, the plurality of press-contact members having leading ends and configured to swing toward the inner peripheral surface and to press contact the outer peripheral surface by an elastic force of the plurality of press-contact members when the blood collection tube is inserted into the hollow part, the blood collection tube holder body including a plurality of tongue-shaped protrusion pieces protruding into the hollow part, such that when the blood collection tube is inserted into the hollow part and the plurality of press-contact members swing toward the inner peripheral surface, the plurality of tongue-shaped protrusion pieces contact the leading ends of the press-contact members, swing toward the inner peripheral surface of the blood collection tube holder body, and assist, with an elastic force of the tongue-shaped protrusion pieces, the press-contact of the plurality of press-contact members with the outer peripheral surface.

2. The blood collection tube holder according to claim 1, wherein the hollow part has a central axis and the plurality of press-contact member includes an arm-shaped part includes a leading end part, the arm-shaped part protruding from the fitting member toward the central axis, a bend part bending from the leading end part toward the inner peripheral surface, and at least one of a first reinforcement piece and a second reinforcement piece, the first reinforcement piece connecting the fitting member and the arm-shaped part, the second reinforcement piece connecting the arm-shaped part and the bend part.

3. The blood collection tube holder according to claim 1, wherein the blood collection tube holder body includes, on the inner peripheral surface, a plurality of contact parts contacting the outer peripheral surface of the blood collection tube inserted into the hollow part.

4. The blood collection tube holder according to claim 3, wherein the blood collection tube includes a flange part and at least two of the plurality of contact parts each include a lock part preventing a fall of the blood collection tube by being locked to the flange part included in the blood collection tube inserted into the hollow part.

5. The blood collection tube holder according to claim 1, wherein the blood collection tube includes a flange part and each press-contact member of the plurality of press-contact member includes a lock part preventing a fall of the blood collection tube by being locked to the flange part included in the blood collection tube inserted into the hollow part of the blood collection tube holder body.

6. The blood collection tube holder according to claim 1, wherein the blood collection tube holder body further includes, on the inner peripheral surface, at least one of a first recessed part in which at least part of the fitting member is housed and a second recessed part in which at least part of a corresponding one of the plurality of press-contact members or a corresponding one of the plurality of tongue-shaped protrusion pieces swinging toward the inner peripheral surface of the blood collection tube holder body is housed.

7. The blood collection tube holder according claim 1, wherein the blood collection tube holder body further includes a connector connectable to a syringe so that the needle tube communicate with the syringe.

8. A blood collection kit comprising:
the blood collection tube holder according to claim 1; and
a blood collection member including a blood collection needle tube configured to pierce a blood vessel, and a holder-side connector, wherein the holder-side connector is connectable to the blood collection tube holder body so that the needle tube communicates with the blood collection needle tube.

9. A blood collection kit comprising:
the blood collection tube holder according to claim 1; and
a connection member including a syringe-side connector and a holder-side connector, wherein the syringe-side connector is connectable to a syringe, the holder-side connector is connectable to the blood collection tube holder body so that the syringe connected to the syringe-side connector communicates with the needle tube.

10. A blood collection kit comprising:
the blood collection tube holder according to claim 2; and
a blood collection member including a blood collection needle tube configured to pierce a blood vessel, and a holder-side connector, wherein the holder-side connector is connectable to the blood collection tube holder body so that the needle tube communicates with the blood collection needle tube.

11. A blood collection kit comprising:
the blood collection tube holder according to claim 3; and
a blood collection member including a blood collection needle tube configured to pierce a blood vessel, and a holder-side connector, wherein the holder-side connector is connectable to the blood collection tube holder body so that the needle tube communicates with the blood collection needle tube.

12. A blood collection kit comprising:
the blood collection tube holder according to claim 4; and
a blood collection member including a blood collection needle tube configured to pierce a blood vessel, and a holder-side connector, wherein the holder-side connector is connectable to the blood collection tube holder body so that the needle tube communicates with the blood collection needle tube.

13. A blood collection kit comprising: the blood collection tube holder according to claim 5; and
a blood collection member including a blood collection needle tube configured to pierce a blood vessel, and a holder-side connector, wherein the holder-side connector is connectable to the blood collection tube holder body so that the needle tube communicates with the blood collection needle tube.

14. A blood collection kit comprising: the blood collection tube holder according to claim 6; and
a blood collection member including a blood collection needle tube configured to pierce a blood vessel, and a holder-side connector, wherein the holder-side connector is connectable to the blood collection tube holder body so that the needle tube communicates with the blood collection needle tube.

15. A blood collection kit comprising: the blood collection tube holder according to claim 7; and
a blood collection member including a blood collection needle tube configured to pierce a blood vessel, and a holder-side connector, wherein the holder-side connector is connectable to the blood collection tube holder body so that the needle tube communicates with the blood collection needle tube.

16. A blood collection kit comprising: the blood collection tube holder according to claim 2; and
a connection member including a syringe-side connector and a holder-side connector, wherein the syringe-side connector is connectable to a syringe, and the holder-side connector is connectable to the blood collection tube holder body so that the syringe connected to the syringe-side connector communicates with the needle tube.

17. A blood collection kit comprising: the blood collection tube holder according to claim 3; and
a connection member including a syringe-side connector and a holder-side connector, wherein the syringe-side connector is connectable to a syringe, and the holder-side connector is connectable to the blood collection tube holder body so that the syringe connected to the syringe-side connector communicates with the needle tube.

18. A blood collection kit comprising: the blood collection tube holder according to claim 4; and
a connection member including a syringe-side connector and a holder-side connector, wherein the syringe-side connector is connectable to a syringe, and the holder-side connector is connectable to the blood collection tube holder body so that the syringe connected to the syringe-side connector communicates with the needle tube.

19. A blood collection kit comprising: the blood collection tube holder according to claim 5; and
a connection member including a syringe-side connector and a holder-side connector, wherein the syringe-side connector is connectable to a syringe, and the holder-side connector is connectable to the blood collection tube holder body so that the syringe connected to the syringe-side connector communicates with the needle tube.

20. A blood collection kit comprising: the blood collection tube holder according to claim 6; and
a connection member including a syringe-side connector and a holder-side connector, wherein the syringe-side connector is connectable to a syringe, and the holder-side connector is connectable to the blood collection tube holder body so that the syringe connected to the syringe-side connector communicates with the needle tube.

21. A blood collection kit comprising: the blood collection tube holder according to claim 7; and
a connection member including a syringe-side connector and a holder-side connector, wherein the syringe-side connector is connectable to a syringe, and the holder-side connector is connectable to the blood collection tube holder body so that the syringe connected to the syringe-side connector communicates with the needle tube.

\* \* \* \* \*